United States Patent [19]

Cleveland

[11] 3,956,308

[45] *May 11, 1976

[54] 5-CHLOROTHIOIMINO IMIDAZOLIDINES

[75] Inventor: James D. Cleveland, Albany, Calif.

[73] Assignee: Chevron Research Company, San Francisco, Calif.

[ * ] Notice: The portion of the term of this patent subsequent to Oct. 22, 1991, has been disclaimed.

[22] Filed: Sept. 5, 1974

[21] Appl. No.: 498,508

Related U.S. Application Data

[62] Division of Ser. No. 251,479, May 8, 1972, Pat. No. 3,843,677.

[52] U.S. Cl. ............................................ 260/309.5
[51] Int. Cl.² .......................................... C07D 49/32
[58] Field of Search ................................. 260/309.5

[56] References Cited

UNITED STATES PATENTS

| | | | |
|---|---|---|---|
| 3,655,689 | 4/1972 | Singer | 260/309.5 |
| 3,766,202 | 10/1973 | Singer | 260/309.5 |
| 3,843,677 | 10/1974 | Cleveland | 260/309.5 |

*Primary Examiner*—Ethel G. Love
*Attorney, Agent, or Firm*—G. F. Magdeburger; D. A. Newell; Raymond Owyang

[57] ABSTRACT

5-Chlorothioimino imidazolidines are produced by the reaction of sulfur dichloride and a 5-imino imidazolidine in the presence of a rate determining amount of an acid acceptor. The 5-chlorothioimino imidazolidines are useful intermediates in the preparation of pesticides.

9 Claims, No Drawings

5-CHLOROTHIOIMINO IMIDAZOLIDINES

This ia a division of application Ser. No 251,479, filed May 8, 1972 U.S. Pat. No. 3,843,677.

FIELD OF THE INVENTION

This invention relates to a process for producing sulfenyl chloride (N-chlorothioimino) derivatives of imino substituted imidazolidines.

Processes for producing sulfenyl chloride derivatives of compounds having active hydrogen atoms substituted on nitrogen are known. E. Kuhle, Synthesis, 561 (1970), discloses the preparation of sulfenyl halide derivatives of sulfoamides and amines. U.S. Ser. No. 45,902 of G. K. Kohn, filed June 12, 1970 now U.S. Pat. No. 3,699,122, discloses the preparation of sulfenyl halide derivative of amides. U.S. Ser. Nos. 88,105 and 88,212 of M. S. Brown and G. K. Kohn, filed Nov. 9, 1970 now U.S. Pat. Nos. 3,679,733 and 3,755,437, respectively, disclose the preparation of sulfenyl halide derivatives of urea and carbamate compounds.

DESCRIPTION OF THE INVENTION

The novel compounds of this invention can be represented by the formula

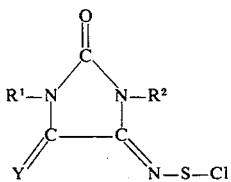

wherein Y is O, S or two hydrogens, $R^1$ and $R^2$ are individually alkyl of 1 to 10 carbon atoms substituted with 0 to 6 halogens of atomic number 9 to 35 (fluorine, chlorine or bromine), cycloalkyl of 3 to 10 carbon atoms substituted with 0 to 6 halogens of atomic number 9 to 35, or aryl of 6 to 12 carbon atoms substituted with 0 to 5 halogens of atomic number 9 to 35, nitro groups, alkoxy groups individually of 1 to 4 carbon atoms, or trihalomethyl wherein the halogen is fluorine or chlorine. Preferably either $R^1$ or $R^2$ will be alkyl or cycloalkyl, optionally substituted as the case may be, and the other of $R^1$ or $R^2$ will be aryl, optionally substituted as the case may be.

Preferably either $R^1$ or $R^2$ will be alkyl of 1 to 6 carbon atoms substituted with 0 to 6 halogen atoms of atomic number 9 to 35 and the other of $R^1$ or $R^2$ will be aryl of 6 to 12 carbon atoms substituted with 0 to 3 halogen atoms of atomic number 9 to 35, nitro groups, or alkoxy groups of 1 to 4 carbon atoms.

The particularly preferred compounds of the present invention are represented by the above formula wherein Y is O or S, either of $R^1$ or $R^2$ is alkyl of 1 to 4 carbon atoms, preferably methyl, and the other of $R^1$ or $R^2$ is phenyl substituted with 0 to 3 (preferably 0 to 1) halogen atoms of atomic number 9 to 35, preferably fluorine.

Representative aliphatic and cycloaliphatic groups which $R^1$ and $R^2$ may represent include alkyl such as methyl, ethyl, propyl, butyl, pentyl, hexyl, heptyl, octyl, nonvl, decyl; cycloalkyl such as cyclopropyl, cyclobutyl, cyclohexyl, cyclodecyl; haloalkyl groups such as chloromethyl, bromomethyl, fluoromethyl, dichloromethyl, trifluoromethyl, 1,2,2,2-tetrachloroethyl, 1,1,2,2,-tetrachloroethyl, trichloromethyl, 2,2-dibromoethyl, 1,1,2-trichloroethyl, 2,2,2-trichloroethyl, 2,4-dichloropropyl, 2,6-difluorohexyl; and halocycloalkyl such as 2-chlorocyclopentyl, 4-bromocyclohexyl, and 2-methyl-3-chlorocyclohexyl.

Representative hydrocarbyl aryl groups which $R^1$ and $R^2$ may represent include phenyl; naphthyl; alkaryl of 7 to 10 carbon atoms such as 2-methylphenyl, 3-methylphenyl, 4-ethylphenyl, 2,4-dimethylphenyl, 3-sec-butylphenyl; and aralkyl of 7 to 10 carbon atoms such as benzyl, 3-phenylpropyl, and 4-phenylbutyl.

Representative substituted aryl groups which $R^1$ and $R^2$ may represent include halo-substituted aryl groups such as 2-fluorophenyl, 4-fluorophenyl, 2-chlorophenyl, 3-chlorophenyl, 3,4-dichlorophenyl, 4-trifluoromethylphenyl, 3-chloro-4-bromophenyl, 2-chloro-4-methylphenyl, 2-fluoro-4-methylphenyl, 4-chlorobenzyl, 4-fluorobenzyl, 2-(2-fluorophenyl)ethyl; alkoxy-substituted aryl groups such as 4-methoxyphenyl, 4-ethoxyphenyl, 4-methoxy-2-methylphenyl, 4-methoxybenzyl; nitro-substituted aryl groups such as 2-nitrophenyl, 4-nitrophenyl and 4-nitrobenzyl; and aryl groups substituted with different substituents such as 2-methoxy-4-chlorophenyl and 2-chloro-4-nitrophenyl. Substituted aryl groups preferably have 1 to 2 substituents. Preferred substituted aryl groups are halo-substituted phenyls, especially those having 1 to 2 fluorine or chlorine substituents.

Representative 5-chlorothioimino-2,4-imidazolidinediones (wherein Y is oxygen) include 1-methyl-3-(4-chlorophenyl)-5-chlorothioimino-2,4-imidazolidinedione, 1-ethyl-3-(2-fluorophenyl)-5-chlorothioimino-2,4-imidazolidinedione, 1-(2-fluorophenyl)-3-methyl-5-chlorothioimino-2,4-imidazolidinedione, 1-(2,4-dichlorophenyl)-3-cyclopentyl-5-chlorothioimino-2,4-imidazolidinedione, 1-(2-fluorophenyl)-3-methyl-5-chlorothioimino-2,4-imidazolidinedione, 1-trichloromethyl-3-(3-chloro-4-bromophenyl)-5-chlorothioimino-2,4-imidazolidinedione, 1-phenyl-3-(1,2,2,2-tetrachloroethyl)-5-chlorothioimino-2,4-imidazolidinedione, 1-cyclohexyl-3-(4-methoxyphenyl)-5-chlorothioimino-2,4-imidazolidinedione, 1-(4-chlorocyclohexyl)-3-(4-nitrophenyl)-5-chlorothioimino-2,4-imidazolidinedione, 1-phenyl-3-(4-trifluoromethylphenyl)-5-chlorothioimino-2,4-imidazolidinedione, 1-methyl-3-methyl-5-chlorothioimino-2,4-imidazolidinedione, 1-benzyl-3-methyl-5-chlorothioimino-2,4-imidazolidinedione, 1-n-butyl-3-(3-phenylpropyl)-5-chlorothioimino-2,4-imidazolidinedione, and 1-methyl-3-α-naphthyl5-chlorothiominino-2,4-imidazolidinedione.

Representative 5-chlorothioimino-imidazolidine 2-one-4-thiones (wherein Y is sulfur) include 1-methyl 3-(2-fluorophenyl)5-chlorothioimino-imidazolidine-2-one-4-thione, 1-methyl-3-methyl-5-chlorothiomino imidazolidine-2-one-4-thione, 1-cyclohexyl-3-phenyl 5-chlorothioimino-imidazolidine-2-one-4-thione, 1-(2 fluorophenyl)-3-trichloromethyl-5-chlorothioimino-imidazolidine-2-one-4-thione, 1-(3-chlorocyclohexyl) 3-(2-nitrophenyl)-5-chlorothiomino-imidazolidine-2-one-4-thione, 1-(3-methoxyphenyl)-3-(2-methyl phenyl)-5-chlorothiominino-imidazolidine-2-one-4-thione, 1-(4-chlorobenzyl)3-(2-methylphenyl)-5 chlorothioimino-imidazolidine-2-one-4-thione, and 1 propyl-3(β-naphthyl)-5-chlorothioimino-imidazolidine 2-one-4-thione.

Representative 5-chlorothioimino-2-imidazolidinon (wherein Y represents two hydrogens) include 1-meth yl-3-(2-fluorophenyl)-5-chloroimino-2-imidazolidinone, 1-methyl-3-(3,4-dichlorophenyl)-5-chloroimino-2-imidazolidinone, 1-(2-fluorophenyl)-3-methyl-5-chloroimino-2-imidazolidinone,1-cyclopentyl-3-(4-methoxybenzyl)-5-chloroimino-2-imidazolidinone, 1-ethyl-3-phenyl-5-chloroimino-2-imidazolidinone, 1-(3,4-dichlorophenyl)-3-4-nitrophenyl-5-chloroimino-2-imidazolidinone, and 1-(α-naphthyl)-3-methyl-5-chloroimino-2-imidazolidinone.

The 5-chlorothioimino imidazolidines are prepared in accordance with the following reaction (1):

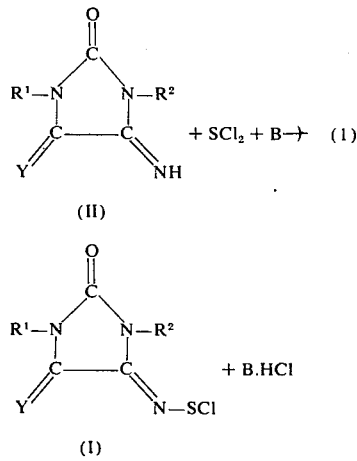

wherein $R^1$, $R^2$ and Y have the same significance as previously defined and B is an acid acceptor.

The acid acceptor is an organic base such as a pyridine compound or a trialkylamine compound. Suitable pyridine compounds are pyridine and pyridine compounds of 6 to 10 carbon atoms and of 1 to 2 alkyl groups such as 2-methylpyridine, 2-ethylpyridine, 3-methylpyridine, 3,5-dimethylpyridine and 2-butylpyridine. Suitable trialkylamines are those wherein the alkyl group contains individually 1 to 4 carbon atoms, such as trimethylamine, triethylamine, tripropylamine and tributylamine.

The sulfur dichloride and the imidazolidine compound are employed in substantially equimolar amounts, e.g., the molar ratio of sulfur dichloride to the imidazolidine compound generally varies from about 0.5:1 to 1:1.5, although molar ratios of sulfur dichloride to the imidazolidine compound of 1.4:1 1.1:1 are preferred. The molar ratios of acid acceptor to sulfur dichloride is also substantially equimolar, e.g., the molar ratio of acid acceptor to sulfur dichloride varies from about 1.2:1 to 1:1.2, although molar ratios of acid acceptor to sulfur dichloride of 1:1 to 1:1.2 are preferred.

In order to produce the 5-chlorothioimino imidazolidine compounds of the invention in high yield, it is essential to react the imidazolidine and sulfur dichloride in the presence of a limited amount of free, uncomplexed (unreacted) acid acceptor. This is suitably accomplished by the addition of the acid acceptor to a substantially equimolar mixture of the imidazolidine and the sulfur dichloride so that the moles of free acid acceptor to the total moles of imidazolidine reactant and 5-chlorothioimino imidazolidine product is less than 0.2:1., preferably less than 0.1:1, and more preferably less than 0.05:1. In other words, during the course of the reaction between the sulfur dichloride and the imidazolidine reactants, there should be at least 5 moles of the reactant and the 5-chlorothioimino imidazolidine product per mole of acid acceptor which is not complexed with hydrochloric acid. Provided that the reaction is conducted with the restricted amount of acid acceptor indicated above, the contacting of the acid acceptor with the mixture of the imidazolidine and the sulfur dichloride can be conducted by a variety of procedures. In one modification, the acid acceptor is added in increments, e.g., dropwise, in an inert diluent, if desired, to a mixture of the imidazolidine and sulfur dichloride in an inert diluent. In another modification, the acid acceptor is added continuously to a mixture of the imidazolidine and sulfur dichloride in an inert diluent.

Suitable inert diluents for the reaction include alkanes of 5 to 10 carbon atoms, such as hexane, isooctane and decane; aromatic compounds such as benzene and chlorobenzene; oxygenated hydrocarbons such as acyclic alkyl ethers. e.g., dimethoxyethane and dibutyl ethers; and cycloalkyl ethers, e.g., dioxane, tetrahydrofuran and tetrahydropyran. Other suitable diluents include nitriles such as acetonitrile and propionitrile; dialkylamides such as dimethylformamide, and dialkylsulfoxides such as dimethylsulfoxide. Preferred diluents are chlorinated hydrocarbons of 1 to 2 carbon atoms, such as methylene dichloride, chloroform, carbon tetrachloride and ethylene dichloride. Generally, the amount of diluent employed ranges from 1 to 50 moles per mole of sulfur dichloride.

The reaction is suitable conducted at a temperature between −20°C. and the boiling point of the diluent, although temperatures between 0° and 50°C. are preferred. The reaction is conducted at or above atmospheric pressure.

In addition to the imidazolidine reactants represented by formula II, the process of the invention is broadly applicable for the preparation of chlorothioimino derivatives of any compound containing an imino substituent, i.e., a —C=N—H group.

UTILITY

The 5-chlorothioimino imidazolidine of the invention are useful intermediates for the preparation of pesticides. For example, the n-chlorothioimino imidazolidine can be reacted with alcohols, mercaptans, ureas, carbamates, amides, anilides, and other compounds having active hydrogen atoms to give the corresponding substitution product (and hydrochloric acid) by the conventional procedures employed for the reaction of sulfenyl halides and compounds having active hydrogen atoms, as disclosed, for example, by E. Kuhle, *Synthesis*, 617 (1971).

The preparation of 5-chlorothioimino imidazolidines of the invention and their conversion into useful herbicides are further illustrated by the following examples.

EXAMPLE 1:
1-(2-fluorophenyl)-3-methyl-5-chlorothioimino-2,4-imidazolidinedione

A 3.7 g (0.048 mole) sample of pyridine was added dropwise to a slurry of 8.84 g (0.04 mole) 1-(2-fluorophenyl)-3-methyl-5-imino-2,4-imidazolidinedione and 4.53 g (0.044 mole) sulfur dichloride in 40 ml of methylene dichloride. At the end of the pyridine addition, the reaction mixture was stirred at about 25°C. for 30 minutes and filtered to give a solution of the 5-chlorothioimino product in methylene dichloride.

EXAMPLE 2:
1-(2-fluorophenyl)-3-methyl-5phenyldithiominio-2,4-imidazolidinedione A solution of about 0.04 mole of 1-(2-fluorophenyl)-3-methyl-5-chlorothioimino-2,4-imidazolidinedione in 40 ml of methylene dichloride was prepared as described in Example 1.

To this solution (cooled in 0°C.) was added dropwise a solution of 3.96 g (0.036 mole) phenyl mercaptan and 3.16 g (0.04 mole) pyridine. The resulting reaction mixture was stirred at about 0°C. for 10 minutes, washed with water, washed with sodium bicarbonate solution, dried over magnesium sulfate and evaporated under reduced pressure to give a yellow solid residue. The residue was taken up in benzene and filtered. The filtrate was chromatographed on silica (benzene elution) to give the imidazolidinedione product as a yellow solid. The product was recrystallized from chloroform/ether to give a light yellow solid, m.p. 89.5–90.5°C. Elemental analysis showed:

|     | Calc. | Found |
| --- | --- | --- |
| S % | 17.7 | 17.3 |
| F % | 5.3 | 5.4 |

EXAMPLE 3:
1-(2-fluorophenyl)-3-methyl-5-n-propyldithioimino-2,4-imidazolidinedione A solution of 6.84 g (0.09 mole) n-propyl mercaptan and 7.9 g (0.1 mole) pyridine in 20 ml of methylene dichloride was added dropwise to a solution of about 0.1 mole of 1-(2-fluorophenyl)-3-methyl-5-chlorothioimino-2,4-imidazolidinedione in 167 ml methylene dichloride at 0°C. After the addition was completed, the reaction mixture was stirred at 0°C. for 30 minutes, washed with water, washed with sodium bicarbonate solution, dried over magnesium sulfate and evaporated under reduced pressure to give a yellowish white residue. The residue was slurried with ethanol and filtered. The filtrate was evaporated to give the product, m.p. 78°–85°C. Elemental analysis showed:

|     | Calc. | Found |
| --- | --- | --- |
| C % | 47.7 | 48.8 |
| H % | 4.3 | 4.0 |
| N % | 12.8 | 13.1 |
| S % | 19.6 | 18.5 |

By a similar procedure, 1-(2-fluorophenyl)-3-methyl-5-chlorothioimino-2,4-imidazolidinedione was reacted with methyl mercaptan and n-butyl mercaptan to give, respectively, 1-(2-fluorophenyl)-3-methyl-5-methyldithiominio-2,4-imidazolidinedione [RE-17681 — m.p. 130°–133°C.; C%, 450.2; H%, 2.9; N%, 13.9 and S%, 19.7] and 1-(2-fluorophenyl)-3-methyl-5-n-butyldithioimino-2,4-imidazolidinedione.

EXAMPLE 4:
1-(2-fluorophenyl)-3-methyl-5-carbethoxymethyldithioimino-2,4-imidazolidinedione 19.7] and 1-(2-fluorophenyl)-3-methyl-5-n-butylidithioimino-2,4-imidazolidinedione [RE-17682 - m.p. 77°–80°C.; C%, 50.6; H%, 4.4; N%, 12.6 and S%, 17.4].

EXAMPLE 4:
1-(2-fluorophenyl)-3-methyl-5-carbethoxymethyldithio-imino-2,4-imidazolidinedione A solution of 10.8 g (0.09 mole) ethyl 2-mercaptoacetate and 7.9 g (0.1 mole) pyridine in 20 ml of methylene chloride was added dropwise to a solution of about 0.09 mole of 1-(2-fluorophenyl)-3-methyl-5-chlorothioimino-2,4-imidazolidinedione in 135 ml methylene chloride at 0°C. The resulting reaction mixture was stirred for about 30 minutes at 0°C., washed with water, washed with sodium bicarbonate, dried over magnesium sulfate and evaporated under reduced pressure to give a yellow solid residue. The residue was taken up in benzene and filtered. The filtrate was diluted with hexane and cooled to 0°C. to crystallize out 15 g of the product as a pale yellow solid, m.p. 79°–82°C. Elemental analysis showed:

|     | Calc. | Found |
| --- | --- | --- |
| S % | 17.3 | 16.6 |
| F % | 5.1 | 5.3 |

By a similar procedure, 1-(2-fluorophenyl)-3-methyl-5-chlorothioimino-2,4-imidazolidinedione was reacted with methyl-3-mercapto-n-propionate to give 1-(2-fluorophenyl)-3-methyl-5-(2-carbomethoxyethyldithioimino)-2,4-imidazolidinedione [RE-17683 - m.p. 81°–84.5°C.; S%, 16.1; F%, 5.3].

EXAMPLE 5:
1-(2-fluorophenyl)-3-methyl-5-methoxythioimino-2,4-imidazolidinedione A solution of 3.2 g (0.1 mole) methanol and 7.9 g (0.1 mole) pyridine in 20 ml of methylene chloride was added dropwise to a solution of about 0.1 mole of 1-(2-fluorophenyl)-3-methyl-5-chlorothioimino-2,4-imidazolidinedione in 100 ml of methylene chloride at 0°C. The resulting reaction mixture was stirred for about 30 minutes at 0°C., washed with water, washed with sodium bicarbonate, dried over magnesium sulfate, and evaporated under reduced pressure to give a yellow solid residue. The solid was washed with isopropyl alcohol to give the product as a pale yellow solid, m.p. 124°–127°C. Elemental analysis showed:

|     | Calc. | Found |
| --- | --- | --- |
| S % | 11.3 | 11.4 |
| F % | 6.7 | 6.5 |

EXAMPLE 6: Herbicide Tests

Pre- and post-emergence herbicidal tests on the imidazolidines prepared in Examples 2–5 were made using the following methods.

Pre-Emergence Test

An acetone solution of the test imidazolidine was prepared by mixing 750 mg. imidazolidine, 220 mg. of a nonionic surfactant and 25 ml. of acetone. This solution was added to approximately 125 ml. of water containing 156 mg. of surfactant.

Seeds of the test vegetation were planted in a pot of soil and the imidazolidine solution was sprayed uniformly onto the soil surface at a dose of 100 micrograms per cm². The pot was watered and placed in a greenhouse. The pot was watered intermittently and was observed for seedling emergence, health of emerging seedlings, etc. for a 3-week period. At the end of this period the herbicidal effectiveness of the imidazolidine was rated based on the physiological observations. A 0 to 100 scale was used; 0 representing no phytotoxicity, 100 representing complete kill.

Post-Emergence Test

The test imidazolidine was formulated in the same manner as described above for the pre-emergence test. The concentration of the imidazolidine in this formulation was 5000 ppm. This formulation was uniformly sprayed on 2 replicate pots of 24-day-old plants (approximately 15 to 25 plants per pot) at a does of 100 micrograms per cm². After the plants had dried, they were placed in a greenhouse and then watered intermittently at their bases as needed. The plants were observed periodically for phytotoxic effects and physiological and morophological responses to the treatment. After 3 weeks the herbicidal effectiveness of the imidazolidinedione was rated based on these observations. A 0 to 100 scale was used; 0 representing no phytotoxicity, 100 representing complete kill.

The results of these tests appear in Table I.

wherein Y is oxygen or sulfur; $R^1$ and $R^2$ are individually alkyl of 1 to 10 carbon atoms substituted with 0 to 6 halogens of atomic number 9 to 35, cycloalkyl of 3 to 10 carbon atoms substituted with 0 to 6 halogens of atomic number 9 to 35, or aryl of 6 to 12 carbon atoms substituted with 0 to 5 halogens of atomic number 9 to 35, nitro groups, alkoxy groups individually of 1 to 4 carbon atoms or 0 to 1 trihalomethyl, wherein the halogen is chlorine or fluorine.

2. Compound of claim 1 wherein either $R^1$ or $R^2$ group is aliphatic or cycloaliphatic and the other $R^1$ or $R^2$ group is hydrocarbyl aromatic.

3. Compound of claim 2 wherein either $R^1$ or $R^2$ is alkyl of 1 to 6 carbon atoms substituted with 0 to 6 halogens of atomic number 9 to 35 and the other $R^1$ or $R^2$ is aryl of 6 to 12 carbon atoms substituted with 0 to 3 halogens of atomic number 9 to 35, nitro groups, alkoxy groups of 1 to 4 carbon atoms.

4. Compound of claim 3 wherein either $R^1$ or $R^2$ is alkyl of 1 to 4 carbon atoms and the other $R^1$ or $R^2$ is phenyl substituted with 0 to 3 halogens of atomic number 9 to 35 or alkaryl of 7 to 10 carbon atoms substituted with 0 to 3 halogens of atomic number 9 to 35.

5. Compound of claim 1 wherein $R^1$ and $R^2$ are alkyl of 1 to 4 carbon atoms.

6. Compound of claim 1 wherein $R^1$ and $R^2$ are phenyl substituted with 0 to 1 halogens of atomic number 9 to 35.

7. Compound of claim 4 wherein $R^1$ is phenyl substituted with 0 to 3 halogens of atomic number 9 to 35 and $R^2$ is alkyl of 1 to 4 carbon atoms.

8. Compound of claim 4 wherein Y is oxygen.

9. A Compound of claim 4 wherein Y is sulfur.

TABLE I

| COMPOUND | Herbicidal Effectiveness Pre/Post | | | | | |
|---|---|---|---|---|---|---|
| | O | W | C | M | P | L |
| 1-(2-fluorophenyl)-3-methyl-5-phenyldithioimino-2,4-imidazolidinedione | 100/10 | 100/10 | 100/10 | 100/100 | 100/100 | 100/100 |
| 1-(2-fluorophenyl)-3-methyl-5-n-propyldithioimino-2,4-imidazolidinedione | 100/20 | 100/20 | 100/20 | 100/100 | 100/100 | 100/100 |
| 1-(2-fluorophenyl)-3-methyl-5-methyldithioimino-2,4-imidazolidinedione | 100/10 | 100/10 | 100/0 | 100/100 | 100/100 | 100/100 |
| 1-(2-fluorophenyl)-3-methyl-5-n-butyldithioimino-2,4-imidazolidinedione | 100/10 | 100/10 | 100/0 | 100/100 | 100/90 | 100/100 |
| 1-(2-fluorophenyl)-3-methyl-5-carbethoxymethyldithioimino-2,4-imidazolidinedione | 100/20 | 95/10 | 95/0 | 100/70 | 100/60 | 100/75 |
| 1-(2-fluorophenyl)-3-methyl-5-(2-carbomethoxyethyldithioimino)-2,4-imidazolidinedione | 100/0 | 100/0 | 100/0 | 100/100 | 100/100 | 100/100 |
| 1-(2-fluorophenyl)-3-methyl-5-methoxythioimino-2,4-imidazolidinedione | 100/30 | 100/30 | 100/15 | 100/100 | 100/80 | 100/90 |

O = Wild Oats (Avena fatua)
W = Watergrass (Echinochloa crusgalli)
C = Crabgrass (Digitaria Sanguinalis)
M = Mustard (Brassica arvensis)
P = Pigweed (Amaranthus retroflexus)
L = Lambsquarter (Chenopodium album)

I claim:
1. Compound of the formula

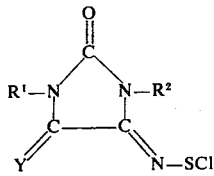

* * * * *